(12) United States Patent
Lin et al.

(10) Patent No.: US 8,618,071 B2
(45) Date of Patent: Dec. 31, 2013

(54) OLIGONUCLEOTIDES FOR SUPPRESSING CANCER CELL INVASION AND MIGRATION

(75) Inventors: Yen-Ju Lin, Taichung (TW); Cheng-Tao Wu, Xindian (TW); Chung-Cheng Liu, Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 13/112,442

(22) Filed: May 20, 2011

(65) Prior Publication Data

US 2011/0288150 A1 Nov. 24, 2011

Related U.S. Application Data

(60) Provisional application No. 61/347,047, filed on May 21, 2010.

(51) Int. Cl.
*A61K 48/00* (2006.01)
*C12N 15/85* (2006.01)
*C07H 21/04* (2006.01)
*C07H 21/02* (2006.01)

(52) U.S. Cl.
USPC .......... 514/44; 435/325; 536/23.1; 536/24.31; 536/24.33; 536/24.5

(58) Field of Classification Search
None
See application file for complete search history.

(56) References Cited

U.S. PATENT DOCUMENTS

| 7,250,289 B2 * | 7/2007 | Zhou ........................ 435/287.2 |
| 7,893,302 B2 * | 2/2011 | Chen et al. .................... 564/384 |
| 2005/0227937 A1 * | 10/2005 | Pavco et al. .................... 514/44 |

OTHER PUBLICATIONS

GenBank Accession No. AB372662, Aug. 2, 2008.

* cited by examiner

*Primary Examiner* — Amy Bowman
(74) *Attorney, Agent, or Firm* — Cesari and McKenna, LLP

(57) ABSTRACT

Provided herein is a method for detection of migratory and invasive cancer cells based on a number of marker nucleic acids differentially expressed in migratory/invasive cancer cells relative to nonmigratory/noninvasive cancer cells. Also disclosed are antisense oligonucleotides of the marker nucleic acids and uses thereof for suppressing cancer cell migration and invasion.

17 Claims, 7 Drawing Sheets

SEQUENCE LISTING

```
<160> NUMBER OF SEQ ID NOS: 14

<210> SEQ ID NO 1
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 1
ugguaccaag gagugggu                                                        19

<210> SEQ ID NO 2
<211> LENGTH: 24
<212> TYPE: RNA
<213> ORGANISM: Artificial sequence
<220> FEATURE:
<223> OTHER INFORMATION: Synthetic oligonucleotide

<400> SEQUENCE: 2
ucuacucuuu cuaggagguu guga                                                 24

<210> SEQ ID NO 3
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 3
ugagguagga gguuguga                                                        18

<210> SEQ ID NO 4
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 4
gccaacuaag ccacagagcc                                                      20

<210> SEQ ID NO 5
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 5
acccacgccu ccaagggaga                                                      20

<210> SEQ ID NO 6
<211> LENGTH: 18
<212> TYPE: RNA
```

```
<213> ORGANISM: Artificial sequence
<220> FEATURE:
<223> OTHER INFORMATION: Synthetic oligonucleotide

<400> SEQUENCE: 6
agccgaaggu uggauauc                                                     18

<210> SEQ ID NO 7
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 7
accccacucc uugguacca                                                    19

<210> SEQ ID NO 8
<211> LENGTH: 24
<212> TYPE: RNA
<213> ORGANISM: Artificial sequence
<220> FEATURE:
<223> OTHER INFORMATION: Synthetic oligonucleotide

<400> SEQUENCE: 8
ucacaaccuc cuagaaagag uaga                                              24

<210> SEQ ID NO 9
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 9
ucacaaccuc cuaccuca                                                     18

<210> SEQ ID NO 10
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 10
ggcucugugg cuuaguuggc                                                   20

<210> SEQ ID NO 11
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 11
ucucccuugg aggcgugggu                                                   20

<210> SEQ ID NO 12
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 12
gauauccaac cuucggcu                                                     18
```

```
<210> SEQ ID NO 13
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 13
auuugauuag ugccuuuacg                                                     20

<210> SEQ ID NO 14
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 14
ucaacaucag ucugauaagc ua                                                  22
```

OLIGONUCLEOTIDES FOR SUPPRESSING CANCER CELL INVASION AND MIGRATION

CROSS REFERENCE TO RELATED APPLICATION

This application claims priority to U.S. Provisional Application No. 61/347,047, filed May 21, 2010, the content of which is incorporated herein by reference in its entirety.

BACKGROUND

Cancer metastasis is a process in which cancer cells spread from one organ/tissue to another. To metastasize, cancer cells must possess two distinct abilities, i.e., motility and invasiveness.

It is of great interest to identify new therapeutic agents that block cancer metastasis via suppression of cancer cell migration and invasion.

SUMMARY

This application is based on the unexpected discovery that a number of RNA molecules, i.e., 5'-UGGUACCAAG-GAGUGGGGU-3' (SEQ ID NO:1), 5'-UCUACUCUUUC-UAGGAGGUUGUGA-3' (SEQ ID NO:2), 5'-UGAGGUAG-GAGGUUGUGA-3' (SEQ ID NO:3), 5'-GCCAACUAAGCCACAGAGCC-3' (SEQ ID NO:4), 5'-ACCCACGCCUCCAAGGGAGA-3' (SEQ ID NO:5), and 5'-AGCCGAAGGUUGGAUAUC-3' (SEQ ID NO:6), suppress cancer cell invasion and migration.

Accordingly, this application features a method for suppressing cancer cell invasion or migration or both by contacting cancer cells (e.g., cells of breast cancer, colon cancer, liver cancer, esophageal squamous carcinoma, squamous carcinoma, brain tumor, or pancreatic cancer) with an effective amount of an oligonucleotide. The oligonucleotide for use in this method includes a nucleotide sequence (i) at least 85% (e.g., 90%, 95%, or 98%) identical to one of SEQ ID NOs:1-6, or (ii) hybridizable to a sequence complementary to one of SEQ ID NOs:1-6 under stringent hybridization conditions. It can be an RNA molecule or a DNA molecule. In one example, the oligonucleotide for use in the method of this invention is a modified RNA molecule having the nucleotide sequence of one of SEQ ID NOs:1-6 and includes one or more modified nucleotides, such as 2'OMe, LNA, 2'MOE, or cyclohexene-containing nucleotides. Optionally, this modified RNA molecule is attached to a cholesterol molecule at its 3' end.

In another aspect, described herein is an isolated oligonucleotide, which is either one of the oligonucleotides described above or a complementary nucleic acid thereof. The term "isolated oligonucleotide" used herein refers to an oligonucleotide substantially free from naturally associated molecules, i.e., the naturally associated molecules constituting at most 20% by dry weight of a preparation containing the oligonucleotide. Purity can be measured by any appropriate method, e.g., column chromatography, polyacrylamide gel electrophoresis, and HPLC. These oligonucleotides are useful in inhibiting cancer invasion and migration, and in manufacturing a medicament for this purpose.

Also provided herein is a method for detecting invasive and migratory cancer cells by (i) providing a sample suspected of containing cancer cells, (ii) detecting in the sample the level of a nucleic acid (e.g., an oligonucleotide) including a nucleotide sequence of one of SEQ ID NOs:7-12, and (iii) assessing whether the sample contains cancer cells that are invasive and migratory. An elevated level of the nucleic acid in the sample relative to that in noninvasive and nonmigratory cells indicates that the sample contains invasive and migratory cancer cells.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The drawings are first described.

DETAILED DESCRIPTION

Figure 1:
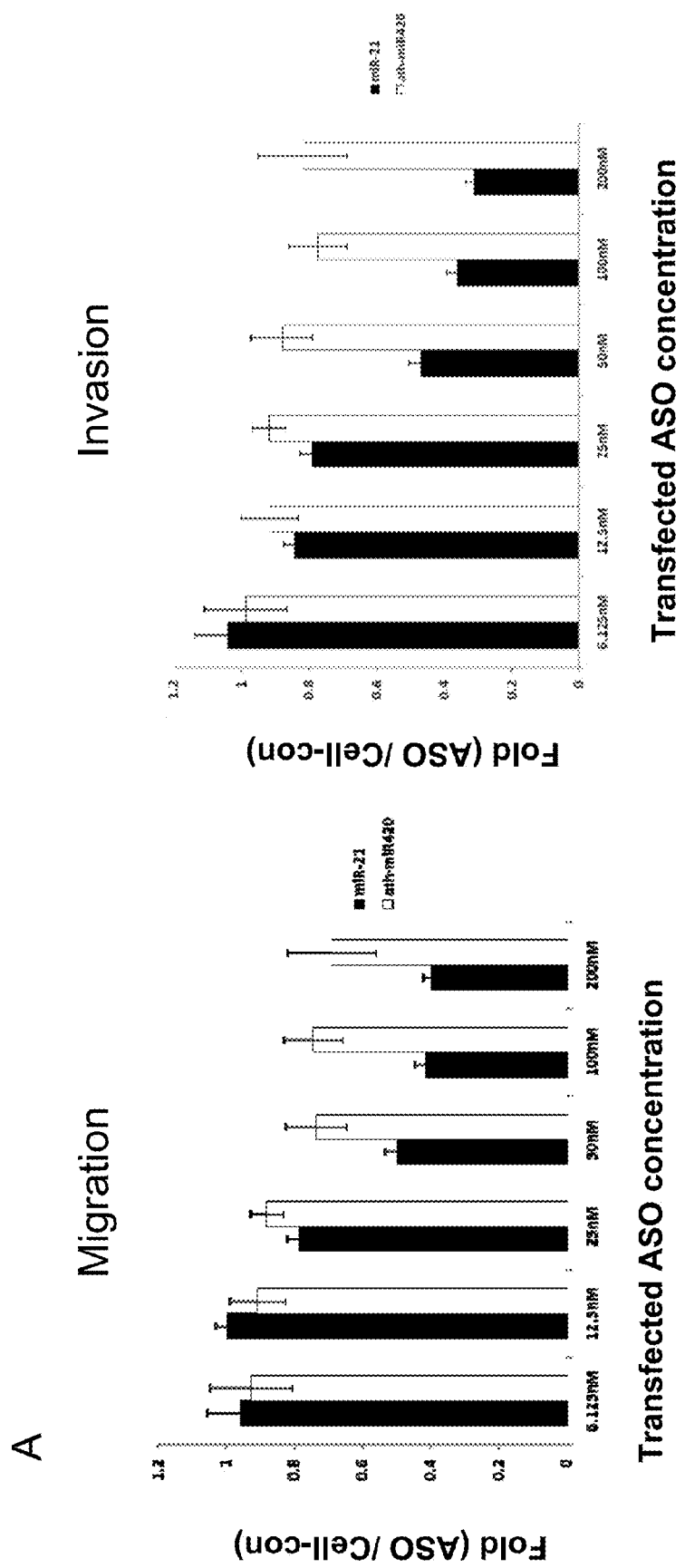
FIG. 1 is a diagram showing suppression of cancer cell migration and invasion by a number of RNA molecules at different concentrations. A: Controls (miR-21 as positive control and ath-miR420 as negative control). B: Suppression of cancer cell migration by RNA molecules "BEL-1" having the nucleotide sequence of SEQ ID NO:1. C: Suppression of cancer cell migration by RNA molecules "BEL-7" having the nucleotide sequence of SEQ ID NO:4. D: Suppression of cancer cell migration by RNA molecules "BEL-8" having the nucleotide sequence of SEQ ID NO:5. E: Suppression of cancer cell migration by RNA molecules "BEL-10" having the nucleotide sequence of SEQ ID NO:6. "ASO"—antisense oligonucleotide.
Figure 1:
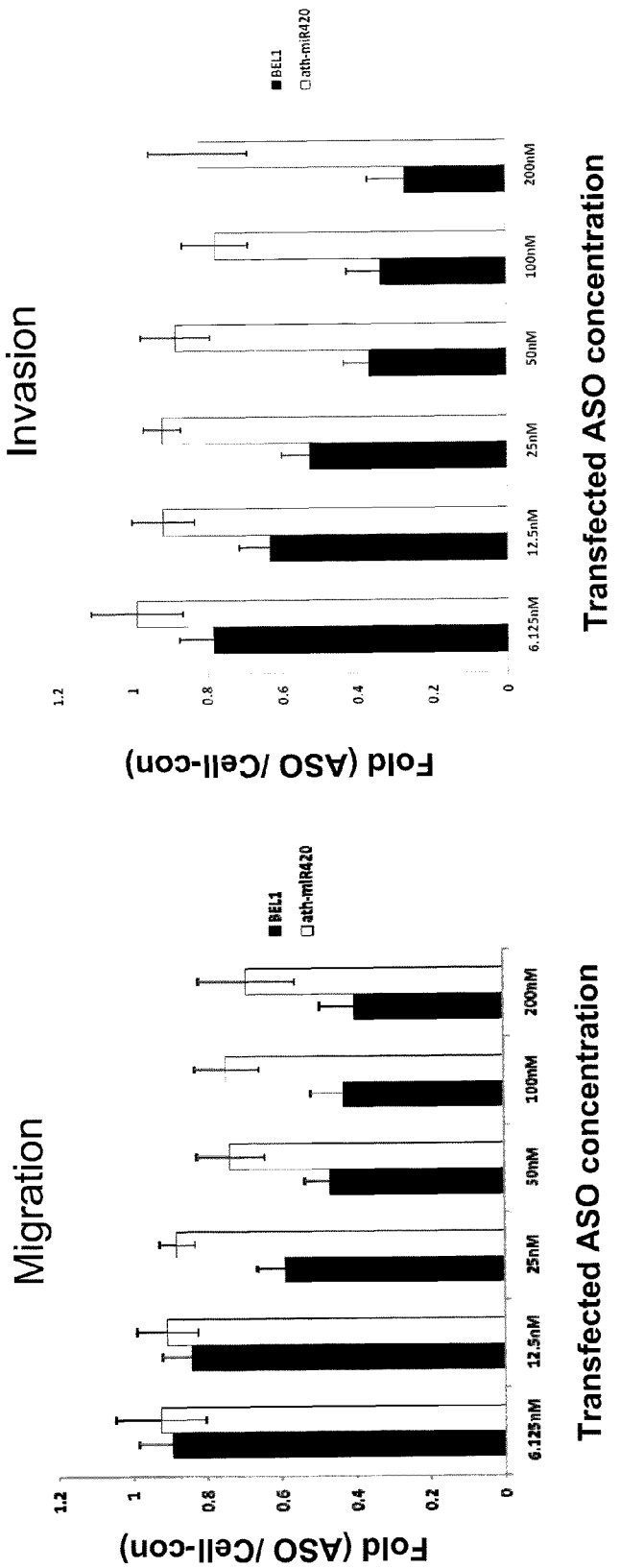
Figure 1:
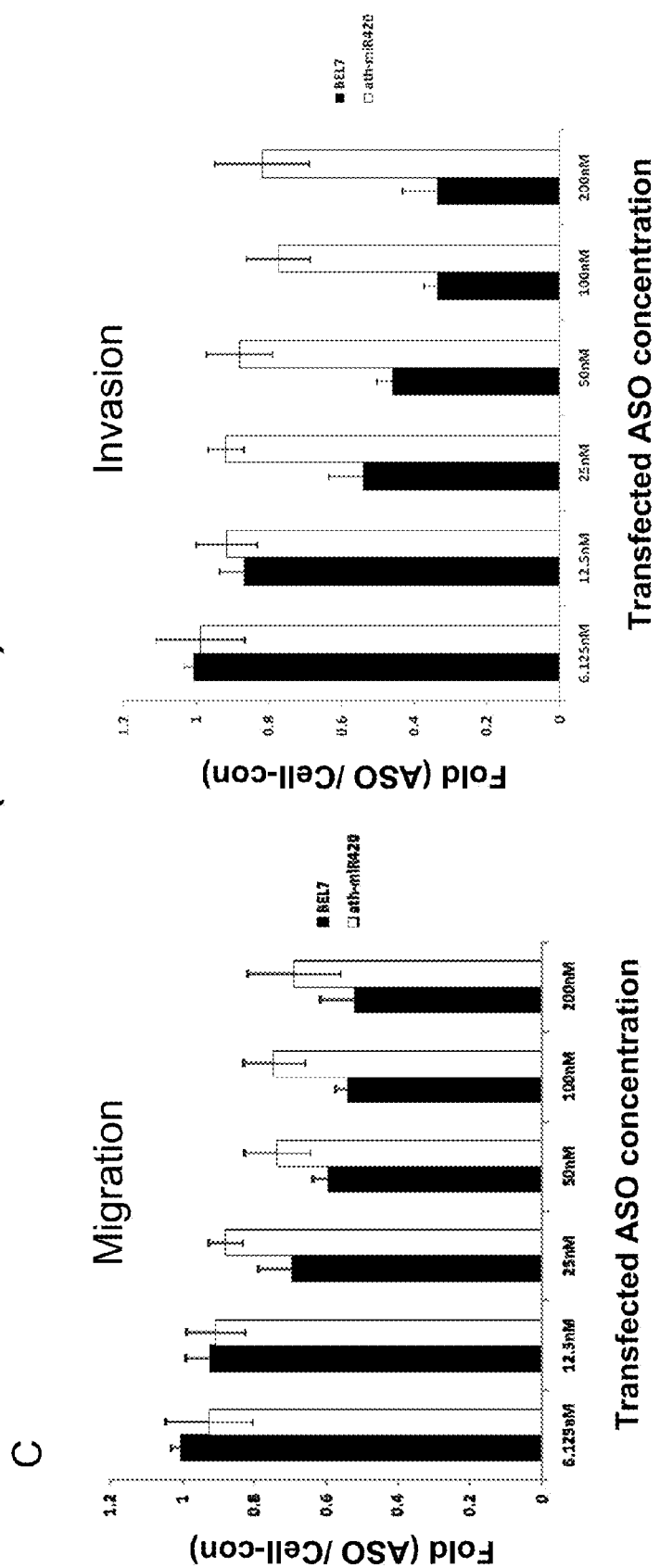
Figure 1:
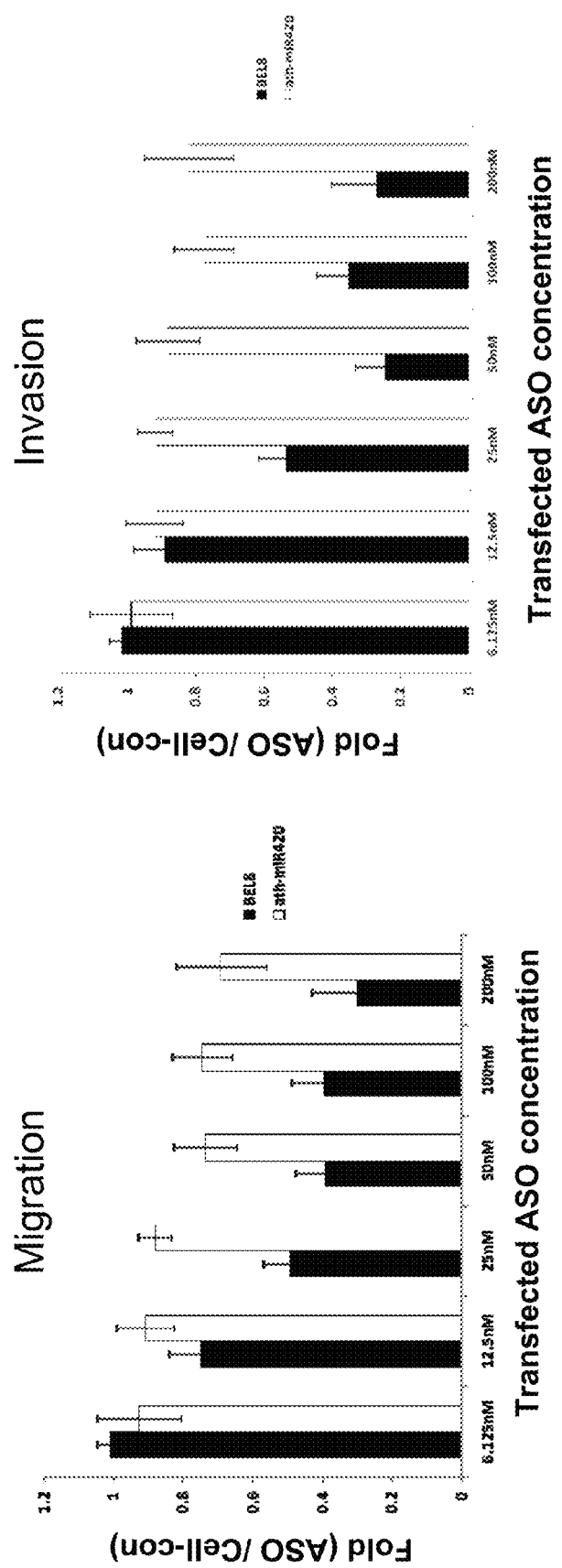
Figure 1:
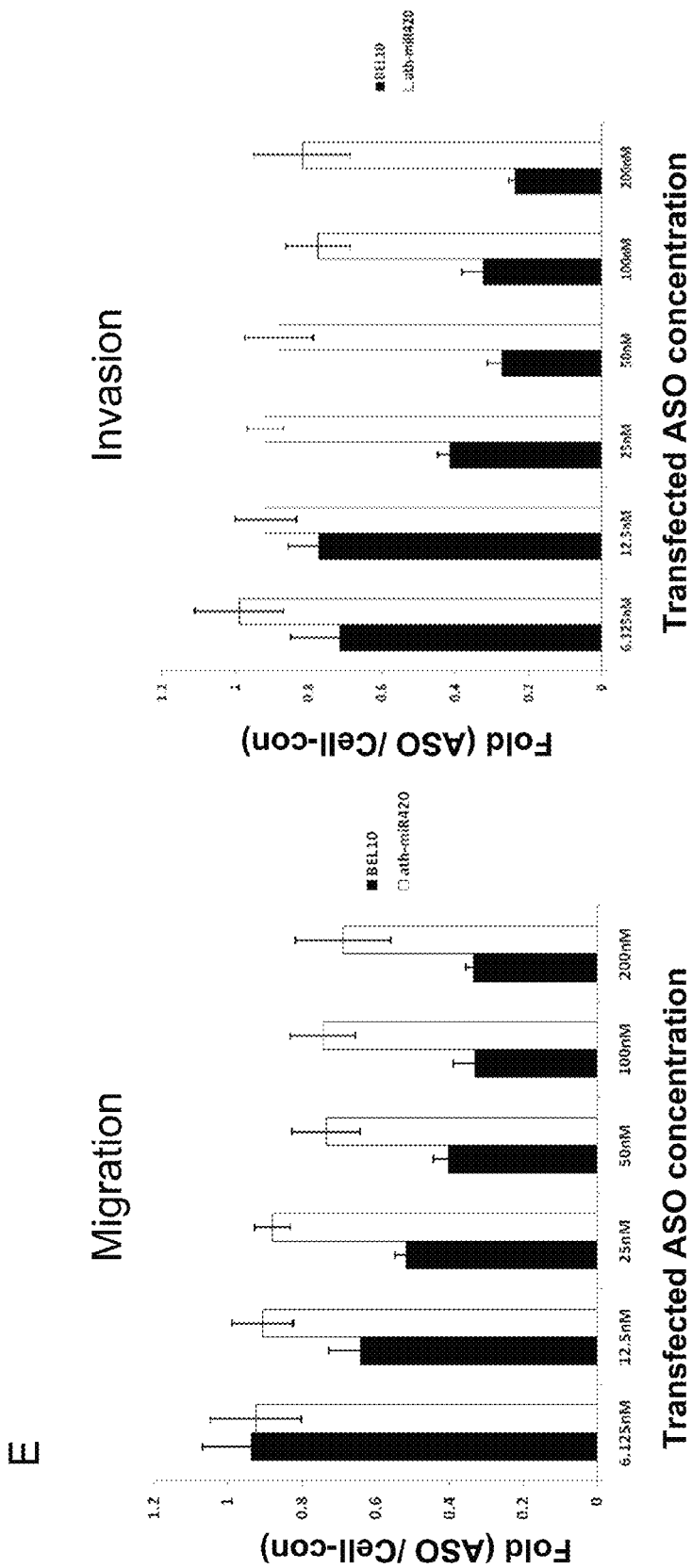

We have identified six small RNAs, listed below, that are differentially expressed in two cancer cells lines that are invasive and migratory as compared to two cancer cell lines that are noninvasive and nonmigratory:

| | |
|---|---|
| 5'-ACCCCACUCCUUGGUACCA-3' | (SEQ ID NO: 7) |
| 5'-UCACAACCUCCUAGAAAGAGUAGA-3' | (SEQ ID NO: 8) |
| 5'-UCACAACCUCCUACCUCA-3' | (SEQ ID NO: 9) |
| 5'-GGCUCUGUGGCUUAGUUGGC-3' | (SEQ ID NO: 10) |
| 5'-UCUCCCUUGGAGGCGUGGGU-3' | (SEQ ID NO: 11) |
| 5'-GAUAUCCAACCUUCGGCU-5' | (SEQ ID NO: 12) |

We have also discovered that antisense oligonucleotides of the above-listed RNA molecules (i.e., oligonucleotides having the nucleotide sequences SEQ ID NOs:1-6) are effective in suppressing cancer cell invasion or migration or both.

Accordingly, described herein is a method of suppressing cancer cell one or both of invasion and migration with an effective amount of an oligonucleotide that includes a nucleotide sequence (i) at least 85% identical to one of SEQ ID NOs:1-6, or (ii) hybridizable to one of SEQ ID NOs:7-12 under stringent hybridization conditions, i.e., low, moderate, or high stringency.

The term "oligonucleotide" used herein refers to a short nucleic acid chain containing up to 100 nucleotides (preferably up to 80, 60, 40, or 25 nucleotides). It can be either an RNA molecule or a DNA molecule. Thus, when an oligonucleotide is described by a nucleotide sequence containing "U," it is not meant to limit that oligonucleotide to an RNA molecule. Indeed, in all of the nucleotide sequences described herein, "U" is interchangeable with "T."

The "percent identity" of two nucleic acids is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215: 403-10, 1990. BLAST nucleotide searches can be performed with the NBLAST program, score=100, wordlength-12 to obtain nucleotide sequences homologous to the nucleic acid molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Stringent hybridization conditions refer to the conditions under which an oligonucleotide will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Typically, stringent conditions include a salt concentration that is less than 1.5 M (e.g., 0.01 to 1.0 M Na ion) at pH 7.0 to 8.3, a hybridization temperature that is at least 30° C. (e.g., 50° C. or 55° C.) for short oligonucleotides (e.g., 10 to 50 nucleotides) and at least about 60° C. for long oligonucleotides (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Optionally, wash buffers may comprise about 0.1% to about 1% SDS. Duration of hybridization is generally less than about 24 hours, usually about 4 to about 12 hours.

Optionally, an oligonucleotide as described above contains non-naturally-occurring nucleobases, sugars, or covalent internucleoside linkages (backbones), e.g., 2'OMe nucleotides, 2'MOE nucleotides, locked nucleic acid (LNA) nucleotides (see, e.g., Singh et al., *Chem Commun* 4: 455-456, 1988; Alexei et al., *Tetrahedron* 54 (14): 3607-30, 1998; and Satoshi et al., *Tetrahedron Lett.* 39 (30): 5401-4, 1998), or cyclohexene-containing nucleotides (see, e.g., Scott Davis et al., *Nucleic Acids Res.* 37(1): 70-77, 2009. Such a modified oligonucleotide confers desirable properties, including enhanced cellular uptake, improved affinity to the target nucleic acid, and increased in vivo stability.

In one example, the oligonucleotide has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the oligonucleotide used in this invention includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., *Helv. Chim. Acta*, 1995, 78, 486-504.

In yet another example, the oligonucleotide includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the oligonucleotides described above can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and U.S. Pat. No. 6,001,311. It can also be transcribed from an expression vector and isolated using standard techniques.

The oligonucleotide or an expression vector for producing such can be mixed with a pharmaceutically acceptable carrier to form a pharmaceutical composition for use in inhibiting cancer cell migration and invasion in a subject in need thereof (e.g., a human cancer patient). "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

Conventional methods, known to those of ordinary skill in the art of medicine, can be used to administer the pharmaceutical composition to the subject via a conventional route, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the oligonucleotide/expression vector and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

To facilitate delivery, the oligonucleotide or vector can also be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide or interfering RNA is encapsulated. Methods for preparing such a micelle, liposome, nanoparticle, or microsphere are well known in the art. See e.g., U.S. Pat. Nos. 5,108,921; 5,354,844; 5,416,016.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the oligonucleotide or vector, causing it to condense (e.g., reduce the size of the oligonucleotide or vector), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

Also provided herein is a method of detecting cancer cells that are migratory and invasive based on the cellular level of a nucleic acid containing a nucleotide sequence of one of SEQ ID NOs:7-12. To perform this method, a cell-containing sample is obtained from a patient suspected of having migratory and invasive cancer cells. RNAs can be isolated from the sample via conventional methods and subjected to analysis (e.g., real-time PCR or microarray) to determine the level of an RNA molecule having the nucleotide sequence of one of SEQ ID NOs:7-12. If the level of the RNA molecule is higher than that in nonmigratory and noninvasive cancer cells (e.g., breast cancer cell MCF-7 or colon cancer cell SW 480), it indicates that the sample contains migratory and/or invasive cancer cells. The result obtained from this method can be replied on for determining the metastatic stage of a cancer patient and for determining a therapeutic strategy suitable for that cancer patient.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

EXAMPLE 1

Elevated Expression of RNA Molecules in Invasive and Migratory Cancer Cells

Expression levels of various RNAs were determined in breast cancer cell lines MDA-MB231 (invasive and migratory) and MCF7 (noninvasive and nonmigratory) and in colon cancer cell lines SW620 (invasive and migratory) and SW480 (noninvasive and nonmigratory). The six RNA molecules listed below were found to be expressed at much higher levels in the invasive and migratory cancer cell lines as compared to the noninvasive and nonmigratory cancer cell lines:

| | |
|---|---|
| 5'-ACCCCACUCCUUGGUACCA-3' | (SEQ ID NO: 7) |
| 5'-UCACAACCUCCUAGAAAGAGUAGA-3' | (SEQ ID NO: 8) |
| 5'-UCACAACCUCCUACCUCA-3' | (SEQ ID NO: 9) |
| 5'-GGCUCUGUGGCUUAGUUGGC-3' | (SEQ ID NO: 10) |
| 5'-UCUCCCUUGGAGGCGUGGGU-3' | (SEQ ID NO: 11) |
| 5'-GAUAUCCAACCUUCGGCU-3' | (SEQ ID NO: 12) |

These six RNA molecules therefore serve as biomarkers for identifying invasive and migratory cancer cells.

EXAMPLE 2

Suppression of Cancer Cell Invasion and Migration by Anti-sense Oligonucleotides Modified RNA molecules having the following sequences were chemically synthesized:

| | |
|---|---|
| 5'-UGGUACCAAGGA GUGGGGU-3', | (SEQ ID NO: 1) |
| 5'-UCUACUCUUUCUAGGAGGUUGUGA-3', | (SEQ ID NO: 2) |
| 5'-UGAGGUAGGAGGUUGUGA-3', | (SEQ ID NO: 3) |
| 5'-GCCAACUAAGCCACAGAGCC-3', | (SEQ ID NO: 4) |
| 5'-ACCCACGCCUCCAAGGGAGA-3', and | (SEQ ID NO: 5) |
| 5'-AGCCGAAGGUUGGAUAUC-3'. | (SEQ ID NO: 6) |

These modified RNAs contained 2'OMe nucleotides and were each attached to a cholesterol molecule at their 3' ends.

Breast cancer cell line MDA-MB231 was used in this study. The cancer cells, suspended in DMEM supplemented with 10% FBS, were seeded at $0.5 \times 10^5$ cells/well in a 24-well plate or at $3 \times 10^5$ cells/well in a 6-well plate. After being cultured at 37° C. with 5% $CO_2$ supply for 24 hours, the cells were transfected with one of the modified RNAs mentioned above, using DharmaFect® Transfection Reagents # 1 (Dharmacon, CA) following the manufacturer's protocol. The transfected cells were incubated at 37° C. with 5% $CO_2$ for 48-72 hours. Existence of the above-mentioned RNAs in the transfected cells were confirmed by quantitative PCR via routine procedures. Anti-miR420 (5'-AUUUGA-UUAGUGCCUUUACG-3', SEQ ID NO:13), and non-transfected MDA-MB231 cell or miR-21 (5'-UCAACAUCAGU-CUGAUAAGCUA-3', SEQ ID NO:14) were used as controls in this study.

160 µl matrigel solution (20 µM) were placed onto the membrane (pore size 8 µm) in a Milicell Cell Culture Inser (Milipore, MA). The Cell Culure Inser was incubated at 37° C. for 30 minutes and then at room temperature for one hour to allow coating of the matrigel onto the membrane. The solution was collected afterwards.

The ability of the above-listed six modified RNAs on cancer cell migration was examined as follows. $5 \times 10^4$ transfected cells were placed in a Cell Culure Inser, the membrane of which has a pore size of 8 (Milipore, MA). The Inser was then placed in a well of a 24-well plate containing 10% FBS as a chemoattractant. The cells were cultured in DMEM or DMEM supplemented with 10% FBS at 37° C. with 5% $CO_2$ for 24 hours to allow cells migration through the membrane of the Inser. The cells remaining on the top surface of the membrane were removed by a cotton swab and the cells migrated to the lower surface of the membrane were fixed with 1% glutaldehyde and stained with crystal violet. After air dry for 24 hours, the dye was extracted with an extraction buffer and the $OD_{570}$ value of the buffer was determined.

Next, the ability of the modified RNAs on cancer cell invasion was tested as follows. The transfected cells were trypsinized, washed with PBS twice, and then suspended in DEME at a cell density of $0.8-1 \times 10^5$ cells/ml. 250 µl of the cell suspension thus formed were placed into the matrigel-coated Cell Culture Inser, which was placed inside a well of a 24-well plate. 750 µl DEME supplemented with 10% FBS (serving as a chemoattractant) were added to the well that holds the Inser. The cells were incubated at 37° C. with 5% $CO_2$ for 24 hours to allow cell invasion into the matrigel-coated membrane. The Culture Inser was then removed from the plate and incubated in 1% glutaraldehyde for 15 minutes to fix cells. The cells remaining on the surface the matrigel-coated membrane were removed and the Culture Inser was placed into a crystal violet solution (0.5%) for cell staining The Culture Inser was then washed with water and placed at room temperature to allow drying of the membrane. 24 hours later, 200 µl Sorenson's buffer was added to the Culture Inser and collected five minutes later. The $OD_{570}$ value, representing the number of the cells invaded into the membrane, was then determined.

RNAs having the nucleotide sequences SEQ ID NO:1-6 significantly suppressed cancer cell migration (data not shown). RNAs having the nucleotide sequences SEQ ID NO:1, 4, 5, and 6 suppressed both migration and invasion of cancer cells in a dose-dependent manner. See FIG. 1, panels A-E.

EXAMPLE 3

Suppression of Cancer Metastasis in Mice by Anti-sense Oligonucleotides

MDA-MB231 cells, suspended in DMEM (without antibiotics) supplemented with 10% FBS and 1% NEAA, were seeded at $2.5 \times 10^6$ cells/10 cm plate. After being cultured at 37° C. with 5% $CO_2$ supply for 24 hours, the cells were transfected with one of the modified RNAs (50 nM) having the nucleotide sequences SEQ ID NO:1, 4, 5, and 6, using DharmaFect® Transfection Reagents # 1 (Dharmacon, CA) following the manufacturer's protocol. The transfected cells were incubated at 37° C. with 5% $CO_2$ for 24 hours. The cell medium was then removed and changed to DMEM with antibiotics, 10% FBS and 1% NEAA, and incubated at 37° C. with 5% $CO_2$ supply for 24 hours. Subsequently, the cells were trypsinized and recovered in suspension in DMEM with 20% FBS. After incubating at 37° C. for 2 hours, the cells were washed twice and resuspended in DMEM.

Figure 2:
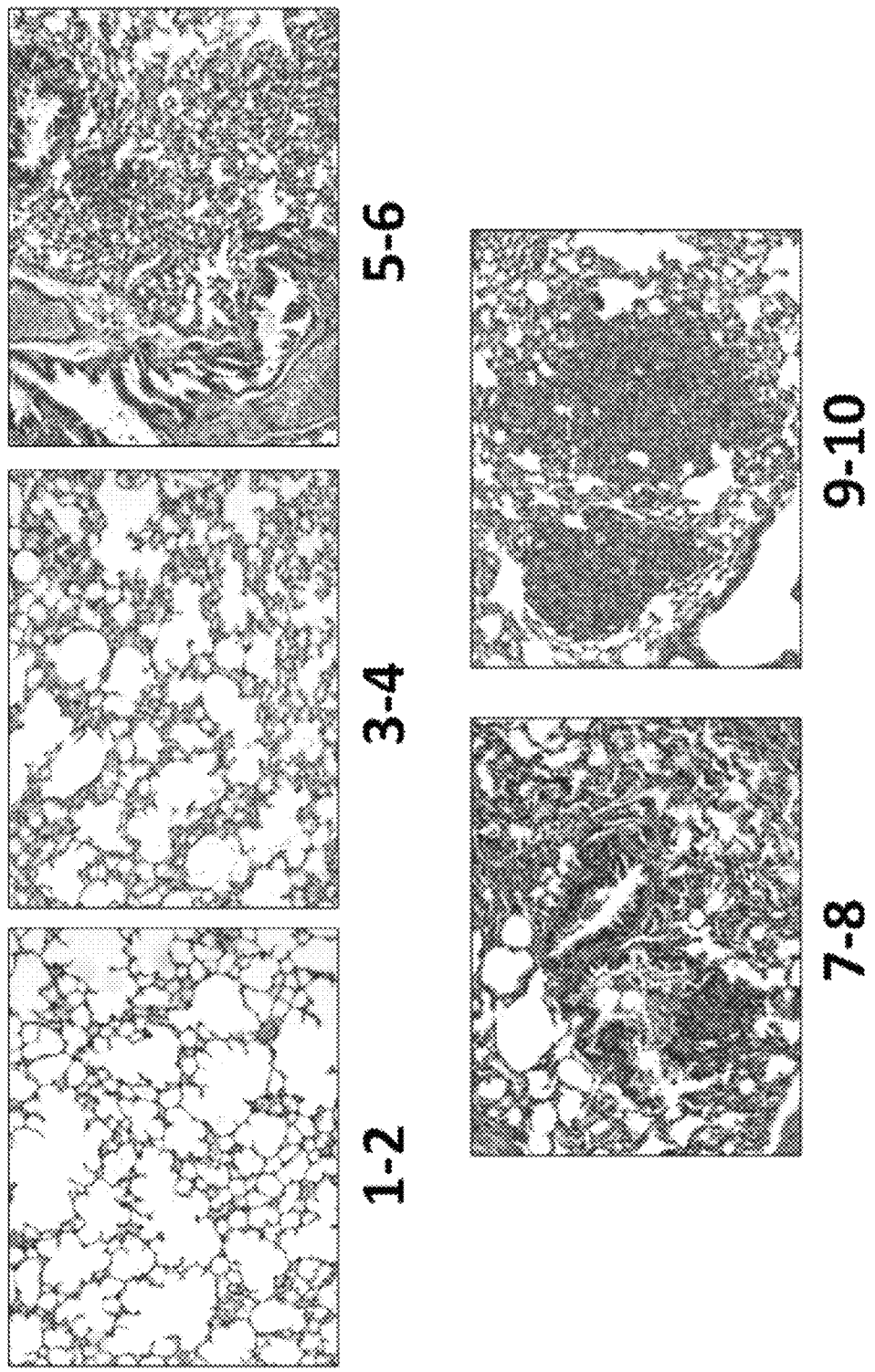
FIG. 2 is a diagram showing criteria for assigning a metastatic score to a tissue.
Figure 3:
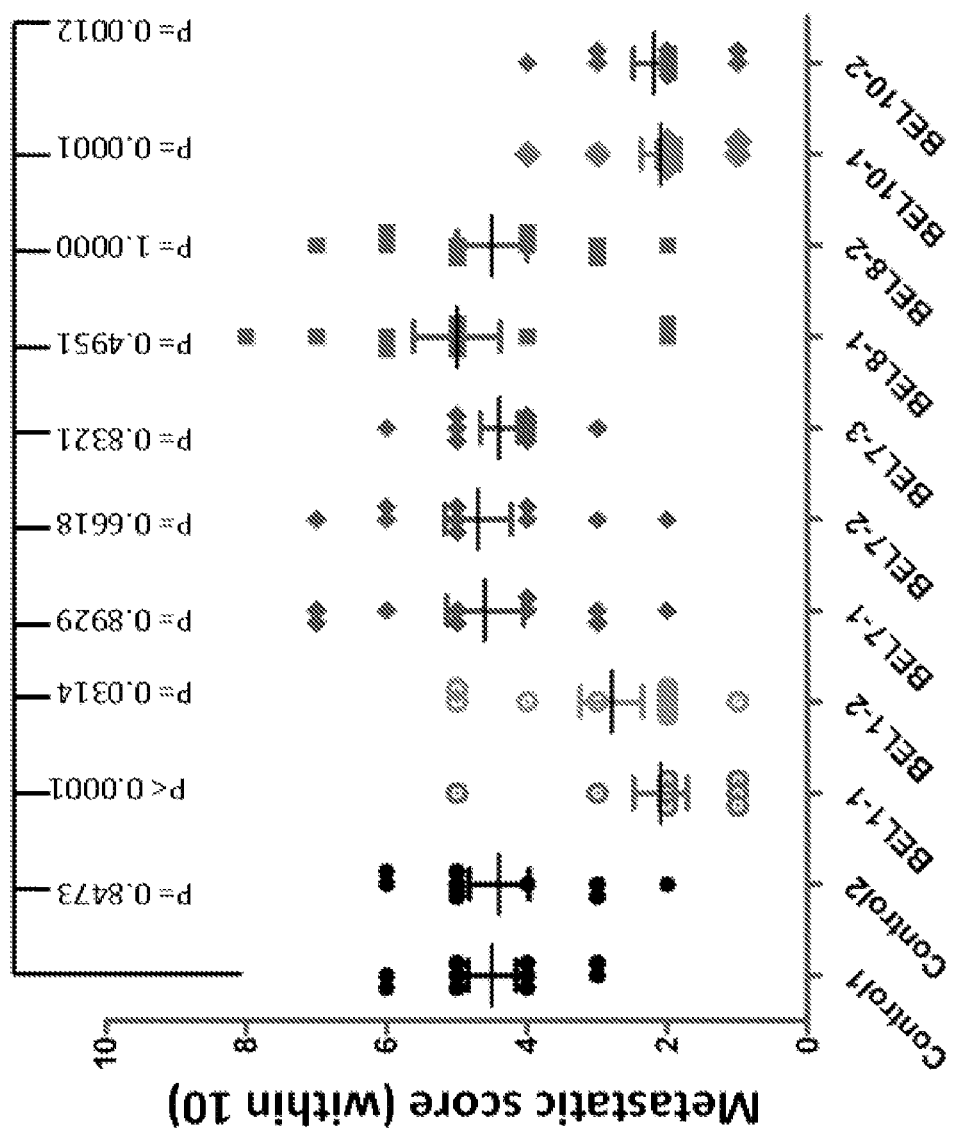
FIG. 3 is a graph showing anti-metastasis effects of various RNA molecules in mice. P<0.05 as compared to the control (determined by t-test). Denoted "–*" means biological replicates in each ASO injection experiment.

Nude mice were injected via tail vein with $1 \times 10^7$ transfected MDA-MB231 cells. Mice injected with MDA-MB231 cells transfected with anti-miR420 were used as negative controls. After 8 weeks, the mice were sacrificed, their lungs removed and prepared for H&E staining. Randomly selected 10 fields per mouse lung tissue were scored for MDA-MB231 cell metastasis (i.e., assigned a metastatic score of between 1-10) according to the criteria shown in FIG. 2. RNAs having the nucleotide sequences SEQ ID NO:1 and 6 in particular exhibited a strong anti-metastasis effect. See FIG. 3.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for contacting cancer cells with an oligonucleotide, comprising contacting the cancer cells with an effective amount of an oligonucleotide, wherein the oligonucleotide includes the nucleotide sequence of SEQ ID NO:6, the oligonucleotide having up to 25 nucleotides.

2. The method of claim 1, wherein the oligonucleotide is an RNA molecule.

3. The method of claim 2, wherein the RNA molecule contains one or more modified nucleotides selected from the group consisting of 2'OMe nucleotide, LNA nucleotide, 2'MOE nucleotide, and cyclohexene-containing nucleotide.

4. The method of claim 1, wherein the 3' end of the RNA molecule is attached to a cholesterol molecule.

5. The method of claim 1, wherein the cancer cells are selected from the group consisting of breast cancer cells, colon cancer cells, liver cancer cells, esophageal squamous carcinoma cells, squamous carcinoma cells, brain tumor cells, and pancreatic cancer cells.

6. The method of claim 1, wherein the contacting step is performed by administering an effective amount of the oligonucleotide to a subject having the cancer cells.

7. The method of claim 6, wherein the oligonucleotide is an RNA molecule.

8. The method of claim 7, wherein the RNA molecule contains one or more modified nucleotides selected from the group consisting of 2'OMe nucleotide, LNA nucleotide, 2'MOE nucleotide, and cyclohexene-containing nucleotide.

9. The method of claim 8, wherein the 3' end of the RNA molecule is attached to a cholesterol molecule.

10. An isolated oligonucleotide, comprising the nucleotide sequence of SEQ ID NO:6, the oligonucleotide having up to 25 nucleotides.

11. The isolated oligonucleotide of claim 10, wherein the oligonucleotide is an RNA molecule.

12. The isolated oligonucleotide of claim 11, wherein the RNA molecule contains one or more modified nucleotides selected from the group consisting of 2'OMe nucleotide, LNA nucleotide, 2'MOE nucleotide, and cyclohexene-containing nucleotide.

13. An oligonucleotide conjugate, the oligonucleotide conjugate comprising (i) an oligonucleotide having up to 25 nucleotides and the sequence of SEQ ID NO:6, and (ii) one or more non-nucleic acid moieties attached to the oligonucleotide.

14. The oligonucleotide conjugate of claim 13, wherein the non-nucleic acid moieties are selected from the group consisting of proteins, carbohydrates, lipids, polyamino acids, micelles, liposomes, nanoparticles, microspheres, chaperon agents, fusogenic agents, and condensing agent.

15. The oligonucleotide conjugate of claim 13, wherein the oligonucleotide is an RNA molecule that contains one or more modified nucleotides selected from the group consisting of 2'OMe nucleotide, LNA nucleotide, 2'MOE nucleotide, and cyclohexene-containing nucleotide.

16. The oligonucleotide conjugate of claim 15, wherein the RNA molecule consists of the sequence of SEQ ID NO:6.

17. The oligonucleotide conjugate of claim 16, wherein one or more cholesterol molecules are attached to the 3' end of the RNA molecule.

* * * * *